United States Patent
Geldmacher et al.

(10) Patent No.: US 10,758,126 B2
(45) Date of Patent: Sep. 1, 2020

(54) DENTAL IRRADIATION DEVICE

(71) Applicant: 3M INNOVATIVE PROPERTIES COMPANY, St. Paul, MN (US)

(72) Inventors: Andreas M. Geldmacher, Dormagen (DE); Korbinian Gerlach, Gauting (DE); Johannes Fink, Bergheim (DE); Stefan K. Welker, Geltendorf (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/564,653

(22) PCT Filed: Mar. 31, 2016

(86) PCT No.: PCT/US2016/025132
§ 371 (c)(1),
(2) Date: Oct. 5, 2017

(87) PCT Pub. No.: WO2016/164238
PCT Pub. Date: Oct. 13, 2016

(65) Prior Publication Data
US 2018/0092543 A1    Apr. 5, 2018

(30) Foreign Application Priority Data
Apr. 10, 2015 (EP) .................... 15163104

(51) Int. Cl.
*A61B 5/00* (2006.01)
*A61C 13/15* (2006.01)
(Continued)

(52) U.S. Cl.
CPC ............ *A61B 5/0088* (2013.01); *A61B 5/065* (2013.01); *A61B 5/067* (2013.01); *A61B 5/7455* (2013.01);
(Continued)

(58) Field of Classification Search
CPC .......................... A61C 19/004; A61C 19/003
See application file for complete search history.

(56) References Cited

U.S. PATENT DOCUMENTS 5,690,486 A    11/1997  Zigelbaum
6,208,788 B1 *  3/2001  Nosov ................. A61C 19/004
                                                            362/554
(Continued)

FOREIGN PATENT DOCUMENTS

EP    0993810 A2 *  4/2000  ........... A61C 19/004
EP    1236444 A1 *  9/2002  ........... A61C 19/004
(Continued)

OTHER PUBLICATIONS

Kratochwilla, Translation for EP-1236444-A1, May 1, 2019, EPO.com (Year: 2002).*
(Continued)

*Primary Examiner* — Sean M Michalski
*Assistant Examiner* — Shannel N Wright
(74) *Attorney, Agent, or Firm* — 3M Innovative Properties Company

(57) ABSTRACT

A dental light irradiation device has sensing means for sensing a change of a position of the device, and an indicator for physically indicating the position change. The invention helps controlling the positioning of the device during use.

10 Claims, 4 Drawing Sheets

(51) Int. Cl.
*A61B 5/06* (2006.01)
*A61B 34/20* (2016.01)
*A61B 17/00* (2006.01)

(52) U.S. Cl.
CPC ... *A61C 19/004* (2013.01); *A61B 2017/00119* (2013.01); *A61B 2034/2048* (2016.02)

(56) References Cited

U.S. PATENT DOCUMENTS

| | | | |
|---|---|---|---|
| 7,766,654 B2 | 8/2010 | Plank | |
| 8,393,037 B2 | 3/2013 | Iwahori | |
| 2004/0228142 A1* | 11/2004 | Takada | A61C 19/004 |
| | | | 362/555 |
| 2004/0248059 A1* | 12/2004 | Katsuda | A61C 19/004 |
| | | | 433/29 |
| 2005/0003323 A1* | 1/2005 | Katsuda | A61B 1/00089 |
| | | | 433/29 |
| 2006/0088798 A1* | 4/2006 | Feinbloom | A61C 19/003 |
| | | | 433/29 |
| 2007/0259309 A1* | 11/2007 | West | A61C 19/004 |
| | | | 433/29 |
| 2009/0021745 A1 | 1/2009 | Tamura | |
| 2009/0087050 A1 | 4/2009 | Gandyra | |
| 2010/0003633 A1* | 1/2010 | Senn | A61C 19/004 |
| | | | 433/29 |
| 2010/0140450 A1* | 6/2010 | Duret | A61C 19/003 |
| | | | 250/205 |
| 2012/0026307 A1* | 2/2012 | Price | A61C 19/004 |
| | | | 348/66 |
| 2012/0052461 A1* | 3/2012 | Hayes | A61C 19/066 |
| | | | 433/29 |
| 2013/0323673 A1* | 12/2013 | Hakomori | A61B 5/0261 |
| | | | 433/29 |
| 2014/0377716 A1* | 12/2014 | Rauscher | A61B 5/0088 |
| | | | 433/29 |
| 2015/0002649 A1 | 1/2015 | Nowak | |
| 2015/0250572 A1 | 9/2015 | Gramann | |
| 2016/0074144 A1* | 3/2016 | Peterson | A61C 19/003 |
| | | | 433/29 |
| 2016/0287364 A1* | 10/2016 | Pauler | A61C 19/004 |
| 2017/0035539 A1* | 2/2017 | Bringley | A61C 19/004 |
| 2018/0263745 A1* | 9/2018 | Tommasini | G01J 1/4257 |

FOREIGN PATENT DOCUMENTS

| | | |
|---|---|---|
| KR | 101371211 | 3/2014 |
| WO | WO 2007-084589 | 6/2007 |
| WO | WO 2014/043488 | 3/2014 |
| WO | WO 2014-068383 | 5/2014 |
| WO | WO 2014-100950 | 7/2014 |
| WO | WO 2014/135589 | 9/2014 |
| WO | WO 2015-148593 | 10/2015 |

OTHER PUBLICATIONS

International Search report for PCT International Application No. PCT/US2016/025132 dated Jun. 20, 2016, 5 pages.
Hese, Stefen, et al., "Sensors for Process and Factory Automation," 6$^{th}$ Edition, ISBN 978-3-658-05866-1; © Springer Fachmedien Wiesbaden 1991, 1993, 2004, 2009, 2011, 2014, 9 pp.
Hering, Ekbert, et al., "Sensors in Science and Technology," http://dnb.d=nb.de, 1$^{st}$ Edition 2012, 14 pp.
Gevatter, Hanse-Jürgen, "Automation Technology," Technical University of Berlin Institute for Microtechnology and Medical Technology, ISBN 978-3-540-66883-1; ISBN 978-3-642-56942-5; © Spring—Verlag Berlin Heidelberg 2000, Spring Verlag Berlin Heidelberg New York 2000, 4 pp.

* cited by examiner

DENTAL IRRADIATION DEVICE

FIELD OF THE INVENTION

The invention relates to a dental light irradiation device, and in particular to a device having sensing means for sensing a change of a position of the device, and an indicator for physically indicating the position change.

BACKGROUND ART

Light-curable or light-hardenable materials are widely used in dentistry for the restoration of teeth, for example for filling a cavity in a tooth. Such materials typically can be made to provide optical characteristics that resemble those of natural teeth, which makes those materials a favored alternative to unpleasant looking amalgam materials, for example.

Light-hardenable materials often include a polymerizable matrix material and filler materials including colorants, and may initially be generally soft or flowable so that they can be applied in a desired location and shape. For example, for restoration of a tooth the dental material may be filled into a tooth cavity and shaped so that the restored tooth resembles a natural tooth. Once the desired shape has been formed, the material may be hardened by exposing it to light of a desired wavelength and for a certain material dependent time period. The light typically activates photoinitiators in the dental material that cause the matrix material to polymerize.

The use of dental materials that are hardenable by blue light of a wavelength of between about 450 and 500 nm has become common in dentistry. Accordingly, dental light irradiation devices used for hardening such dental materials typically emit light at such wavelengths and typically enable the device to automatically control the light emission for only a pre-selected or pre-selectable time period. Such dental light irradiation device, for example, is available from 3M ESPE, Germany, under the trade designation Elipar™ S10 LED Curing Light.

Normally irradiating a dental material causes that portion of the dental material to harden, which is exposed to sufficiently intense light emitted from the device. Therefore, appropriate irradiation of the dental material to be hardened is critical for the quality and durability of the hardened dental material.

Typically devices of the prior art can operate at different operation times and/or at different intensities to control appropriate hardening of the dental material. Thus too long or too short exposure of dental can typically be controlled. However there is still a need for a device which minimizes the dependency between quality of the filling and handling of the device. Further it is still desirable to provide a device that allows easy handling for appropriately hardening dental materials in different situations.

SUMMARY OF THE INVENTION

The invention relates to a dental light irradiation device as defined in claim 1. The light device comprises sensing means for sensing a change of a position of the device, and an indicator for physically indicating the position change.

The invention is advantageous in that it helps maximizing the quality and durability of hardened dental materials. Further, the invention facilitates the use of the device because it is configured to guide a user to keep the device in an appropriate position during hardening dental material.

For the purpose of the present specification "blue light" refers to light having a wavelength within a range of about 430 nm (nanometers) and about 490 nm and a peak wavelength within a range of about 444 nm and 453 nm. Further such blue light preferably substantially does not comprise light at wavelengths outside the range of about 430 nm and about 490 nm. For example at least 90%, more preferably 95% of the light quantity emitted from the device is formed by blue light having a wavelength within a range of about 430 nm and about 490 nm.

In one embodiment the indication of a position change is an alert for the user to reposition the light device toward about the position from which the device was changed in position.

In an embodiment the device is configured such that the position change is indicated upon the position change exceeding a predetermined threshold. For example the device may be configured such that the position change is only indicated upon the position change exceeding a predetermined threshold. This means that slight position changes are possible without the device indicating any position change. This allows for typical position changes from normal manual operation of the device without activating any alert.

In a further embodiment the sensing means comprises a sensor for measuring a physical quantity. Such a sensor may be a photo diode or an array of photo diodes, for example. The sensor is preferably connected to a controller of the device. The controller is preferably configured to interpret a change of the physical quantity as a position change of the device. Such a physical quantity may be a light intensity as detectable by a photo diode. The controller may be configured to interpret the change of the physical quantity based on monitoring a magnitude of the physical quantity over time. For example a magnitude of the physical quantity change may converted into a magnitude of the position change.

In one embodiment in operation for irradiating light, the light device:
(i) causes the sensor to measure a series of physical quantities $Q_1$ to $Q_n$;
(ii) compares a reference value and a determined value, wherein the reference value is derived from one or more of the measured physical quantities $Q_1$ to $Q_{n-1}$ and the determined value is derived from $Q_n$; and
(iii) activates the indicator or leaves the indicator inactivated depending on the result of the comparison.

For example the light device may in step (ii) compare a reference value and a determined value, wherein the reference value is derived from measured physical quantities $Q_k$ to $Q_n$ with k<n and the determined value is derived from $Q_n$. Further, the determined value may be derived from measured physical quantities $Q_j$ to $Q_n$ with $1 \leq k < j \leq n$.

The term "derived" with respect to "derived from one or more of the measured physical quantities" may for example comprise the calculation of an average, the calculation of a factor, the calculation of an offset, or a combination thereof.

In a further embodiment the device has a memory for storing at least two of the quantities $Q_1$ to $Q_n$. The device may be further configured to store the threshold. The threshold may be user determinable or selectable. For example the device may have an input for selecting the threshold out of a predetermined range of thresholds. Such an input may comprise a control knob or a button.

In one embodiment the device is adjustable in its sensitivity. For example the device may indicate a position change only upon recognizing two or more position changes in sequence. Therefore the device may further have a sensitivity switch for adjusting the sensitivity.

In a further embodiment the device further comprises a database holding one or more patterns that are indicative or non-indicative of a position change. The patterns are preferably in the form of data sets of physical quantities. The device is preferably configured to account for at least one of the patterns during comparing the reference value and the determined value. Such a pattern may comprise a series of physical quantities as they typically occur during manually operating the device. For example, the pattern may reflect greater changes in position shortly after activation of the device. Such greater changes may result from the operation of the on/off button of the device by the user.

In a further embodiment the device adapts the reference value based on the determined value and/or one of the physical quantities $Q_1$ to $Q_n$. Thereby the device auto-adjusts the light device to a current position as a basis for sensing a change of a position. The device may for example assume a physical quantity $Q_{n-1}$ selected from among the series of physical quantities of $Q_1$ to $Q_n$ as reference value. In more particular, the device may assume the respective quantity $Q_{n-1}$ as reference value and may compare the quantity $Q_n$ plus/minus the threshold with the reference value. In case the reference value is outside a range of $Q_n$ plus/minus the threshold a change in position may be determined.

In one embodiment the sensing means comprises a photodiode or an acceleration sensor or a gyroscope.

In one embodiment the sensing means comprises a camera for capturing images. The camera may be connected to a controller of the device that is configured to interpret a change between two or more images as a position change of the device. The camera is preferably based on a CCD or CMOS imaging device.

In one embodiment the indicator comprises a vibrating alert device, an audio or visual feedback device, or a combination thereof. A vibrating alert may be based on a motor that is connected for driving an out-of-balance weight.

In one embodiment the light device comprises a communication interface, such as a radio communication interface. One commonly known radio communication interface as it may be used with the light device of the invention is the Bluetooth® interface. The communication interface may be used to transmit information about a position change of the device. In this embodiment an external alarm device that is connectable via the communication interface to the light device may physically indicate the position change of the light device. Such an alarm device may be a customized device or a standard device like a computer, tablet or cell phone. Further, in this embodiment the indicator may be formed of only the communication interface or the device may have an additional indicator like a vibrating alert device, an audio or visual feedback device, or a combination thereof.

The light device of the invention preferably comprises a light source for emitting blue light. Such a light source is preferably formed by a single high power LED. The device may further comprising a light guide forming at one end a light input and a light output on an opposite end. The light guide is preferably configured for guiding light incident on one of the ends to the respective other one of the ends via reflection, in particular via total reflection. The light guide preferably comprises a plurality of optical fibers extending parallel between the light input and the light output.

In one embodiment the sensing means and the light source are arranged adjacent the light input of the light guide. Those fibers of the light guide which guide light from the light output toward the light input and toward the sensing means preferably also guide light from the light source toward the light output, in operation of the device. Thus, the same fibers can be used for emitting and receiving light.

In a further embodiment the sensing means are arranged adjacent the light output of the light guide, whereas the light source is arranged adjacent the light input.

In still a further embodiment the sensing means and the light source are arranged adjacent a free end of light tip. Such a light device typically has no light guide, but an elongated light tip which forms a light output at its free end.

DETAILED DESCRIPTION OF THE INVENTION

Figure 1:
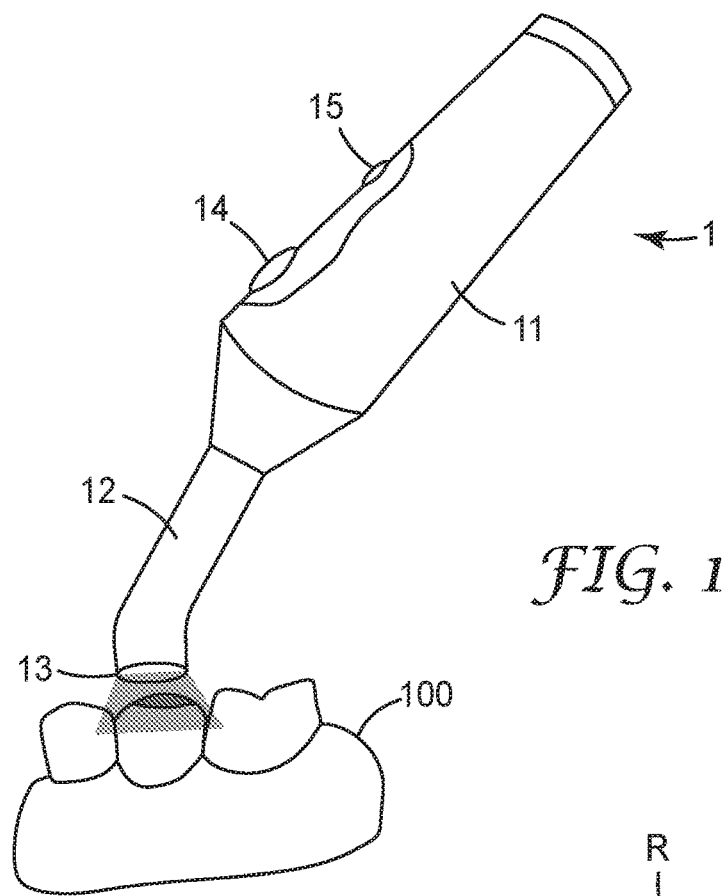
FIG. 1 is a perspective view of a light device according to an embodiment of the invention.

FIG. 1 shows an exemplary dental light device 1 according to the invention. The light device 1 has a body 11 and a light guide 12. The Light guide 12 is configured for guiding light which is emitted from a light source (not shown) within the body 11 toward a light output 13 of the light guide 12. The light guide 12 is preferably formed of a multiplicity of fibers which extend in a parallel fashion between ends of the light guide 12. One of the ends of the light guide 12 forms the light output 13 which in the example forms a clear planar surface. The opposite other end (not shown) of the light guide 12 forms a light input. Accordingly the light guide 12 is configured to guide light received in the light input toward the light output 13.

In the illustrated example the light device 1 is used for irradiating a light hardenable dental material in a tooth of a patient's dentition 100. The light device 1, in particular the light source, is configured to emit blue light.

The light device 1 further has a main button 14 for switching the device 1 on or off, as well as a selector button 15 for pre-selecting a time-period of a light emitting cycle. A light emitting cycle is initiated upon operation of the main button 14 and results in the light device 1 to automatically emit light for the pre-selected time-period until it automatically deactivates. Premature switching the light device 1 off is enabled via operating the main button 14 during a light emitting cycle.

The light device 1 is battery powered. Therefore the device 1 can be operated cord free. The battery can be recharged by connecting the light device 1 with a charger (not shown).

Figure 2:
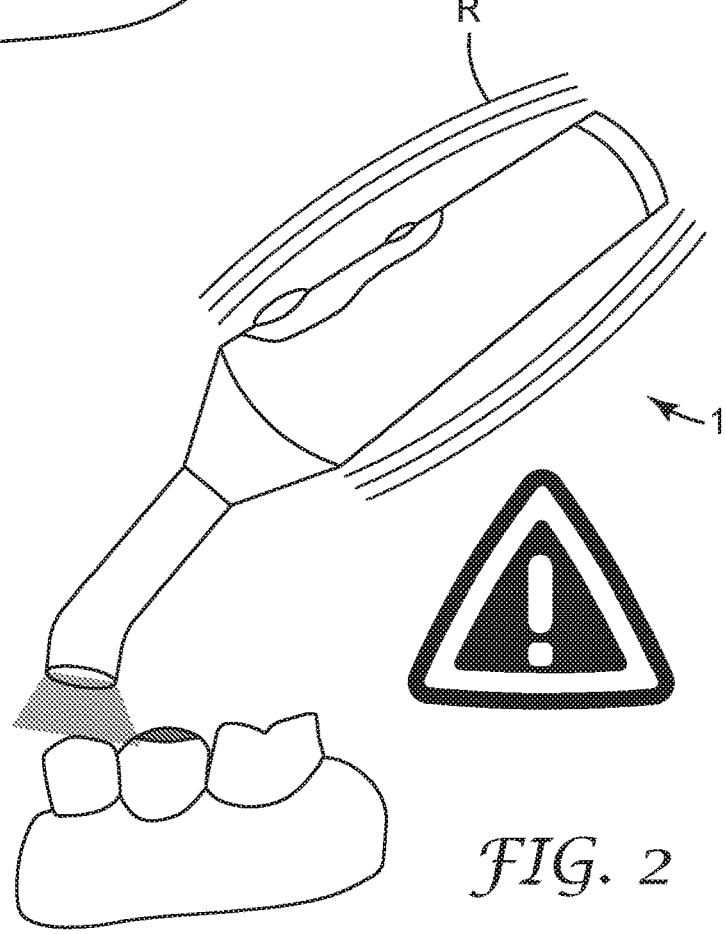
FIG. 2 is a perspective view of the device shown in FIG. 1 in a different operation situation.

In FIG. 2 the light device 1 is shown in a different position relative to the position shown in FIG. 1. FIG. 2 particularly illustrates a situation in which the light device 1 has just been repositioned. In response to the repositioning the light device 1 indicates the position change, in the example by a vibration alert (indicated as "R" in the Figure). The change in position is sensed by sensing means, an example of which is illustrated in FIG. 3.

Figure 3:
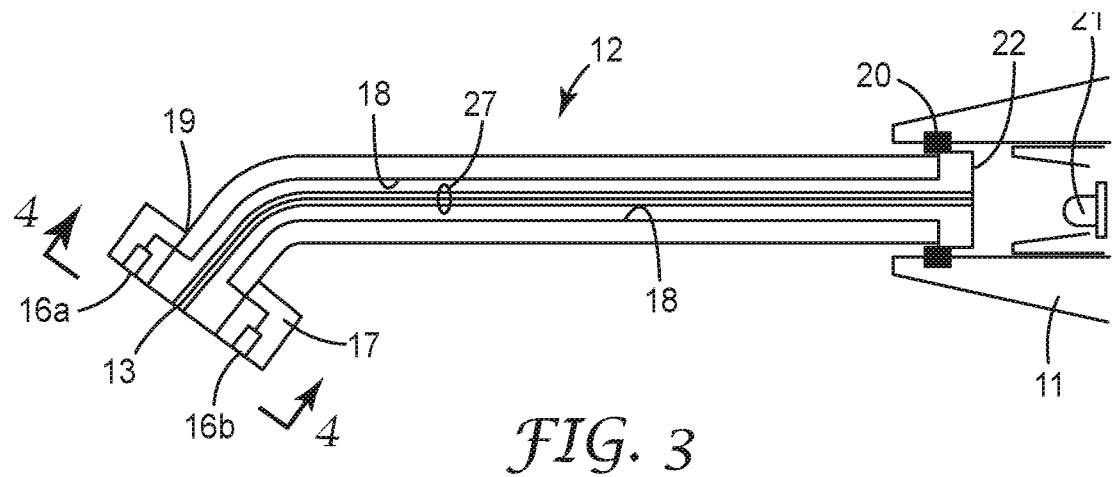
FIG. 3 is a cross-sectional view of a portion of a light device according to an embodiment of the invention.
Figure 4:
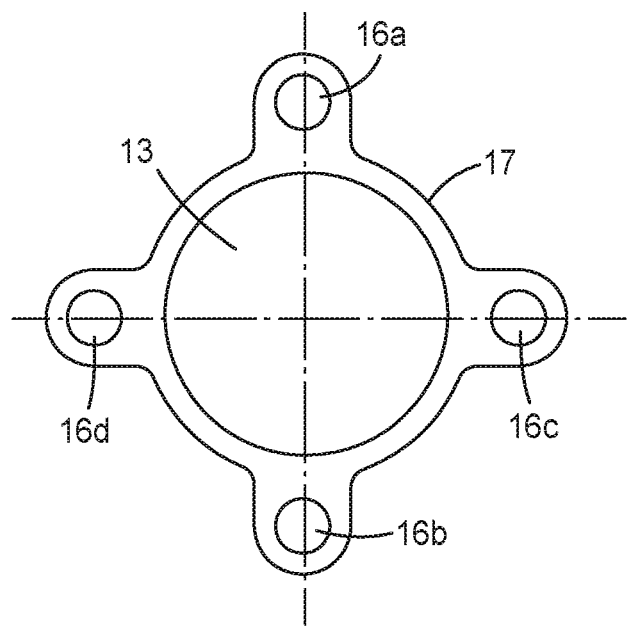
FIG. 4 is a top view onto a light output of a light guide of the device shown in FIG. 3.

FIG. 3 shows the light guide 12 in more detail. A series of photo diodes 16*a*, 16*b* is arranged adjacent the light output 13 of the light guide 12. The photo diodes 16*a*, 16*b* are preferably arranged circumferentially around the perimeter of the light output 13. Although in the cross-sectional view of FIG. 3 only two photodiodes are illustrated, the light device of the example has four photo diodes 16*a*, 16*b*, 16*c* and 16*d* which are uniformly distributed around the perimeter of the light output 13, as shown in more detail in FIG. 4. The photo diodes 16*a*-16*d* are arranged in a ring 17 which is preferably detachably mounted on the light guide 12, for example by a press fit.

Electrical conductors 18 for connecting the photo diodes 16*a*-16*d* are provided at the outer surface of the light guide 12, for example in the form of electrically conductive coatings such as (transparent) indium tin oxide coatings, (non-transparent) aluminum coatings or any other appropriate electrically conductive material. The ring 17 may be furnished with sliding contacts 19 for connecting with an end of the electrical conductors 18. Further sliding contacts 20 may be arranged at a mouth piece of the body 11, which is adapted for removably receiving the light guide 12 within the mouth piece. The sliding contacts 20 are adapted for connecting with another end of the electrical conductors 18. A light source 21, in the example a high power LED, is arranged in proximity to the light input 22 of the light device 1. The light guide 12 is formed of a plurality of optical fibers 27 extending parallel between the light output 13 and the light input 22. Although FIG. 3 shows three optical fibers 27 for simplicity, light guide 12 may include more optical fibers than shown.

Figure 5:
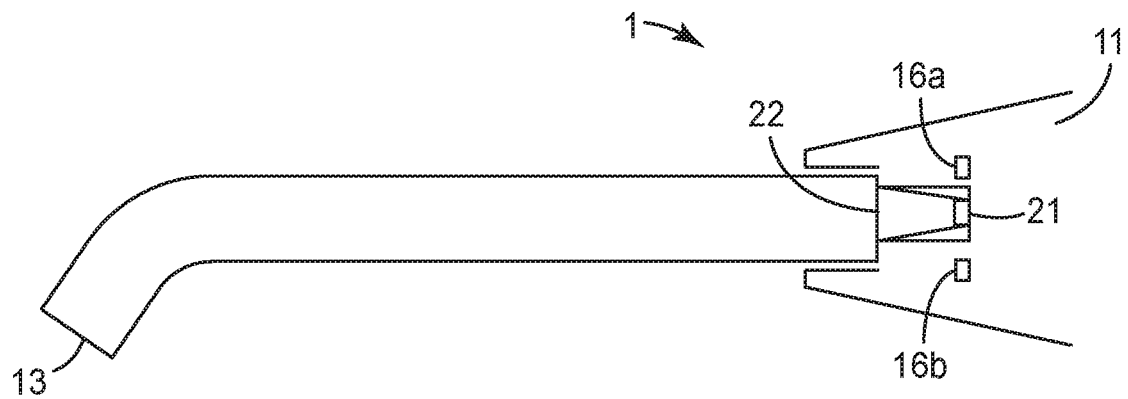
FIG. 5 is a cross-sectional view of a portion of a further light device according to an embodiment of the invention.

FIG. 5 shows a further embodiment of the light device 1 in which the sensing means are arranged within the body 11 of the light device 1. In this embodiment the photo diodes 16*a*-16*d* are arranged around the light source 21. The photo diodes 16*a*-16*d* are arranged uniformly on a (virtual) concentric circle around the light source 21. Thus, the light source 21 and the photo diodes 16*a*-16*d* are arranged within the body 11 of the light device 1 and are optically coupled with the light guide 12. This means that light emitted from the light source 21 is guided from the light input 22 toward the light output 13. Further, light impinging on the light output 13 is guided toward the photo diodes 16*a*-16*d*. It is noted that the same fibers of the light guide are used for simultaneously guiding light from the light input 22 toward the light output 13 and from the light output 13 toward the light input 22.

With such a configuration, the light source 21 and the photo diodes 16*a*-16*d* are protected from a contact with the intra-oral environment of a patient during use of the device 1. Further, because the light guide 12 of this embodiment does not have any electrical elements the light guide 12 can be disinfected at high temperatures and/or using aggressive disinfectants.

In the example the light source 21 and the photo diodes 16*a*-16*d* are configured as so-called surface mounted devices (SMD) and mounted on a common generally planar circuit board. The photo diodes 16*a*-16*d* may be optically shielded from the light source 21 to avoid that light of the light source 21 affects the sensing of the light source 21. Such an optical shield may be formed by a circumferential ring around the light source 21 which extends over or beyond the light exit surface of the light source 21. Preferably the photo diodes 16*a*-16*d* are arranged such that the light entry sides of the photo diodes 16*a*-16*d* are located outside the light cone emitted from the light source 21.

Figure 6:
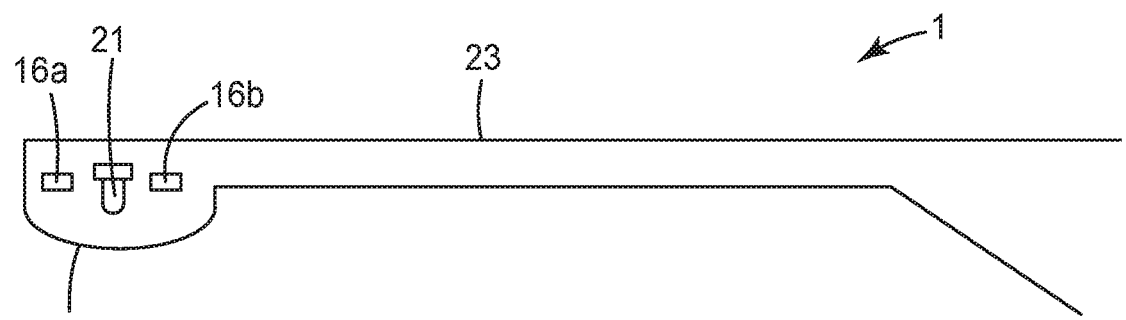
FIG. 6 is a cross-sectional view of a portion of a light device according to still a further embodiment of the invention.

FIG. 6 shows an embodiment of a light device 1 which has a light tip 23, a free end of which forming the light output 13. The light source 21 and the sensing means, in particular the photo diodes 16*a*, 16*b*, are arranged in immediate proximity behind the light output 13. The light output 13 may be formed by a clear cover, for example a glass cover, which sealingly closes an opening in the light tip 23. Further, the light output 13 may be formed by a clear portion of a monolithic light tip 23, for example a glass light tip 23.

Figure 7:
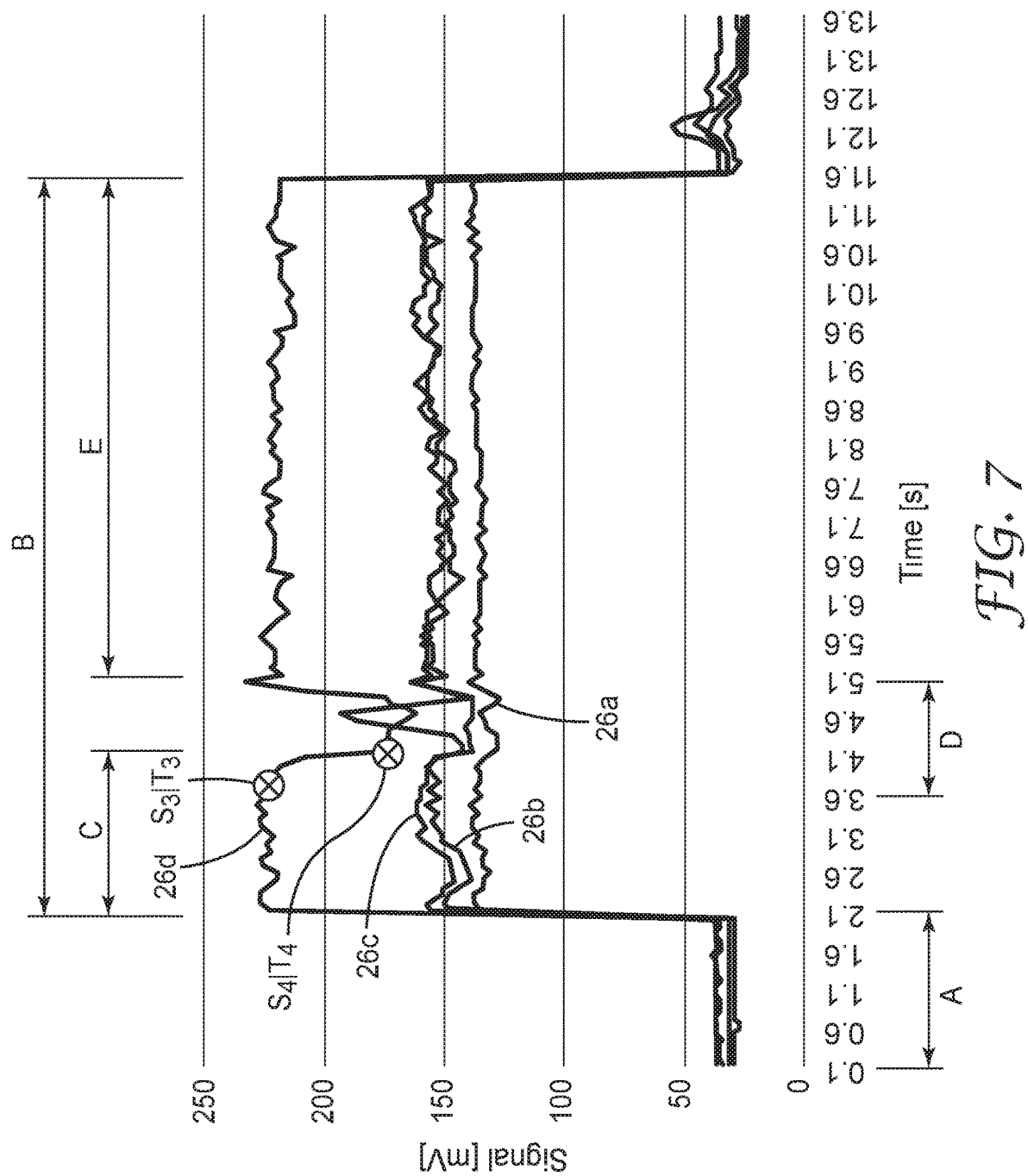
FIG. 7 is a diagram illustrating a function of a light device according to an embodiment of the invention.

FIG. 7 shows a diagram illustrating the function of the sensing means. The diagram represents in the vertical dimension a voltage signal in mV as generated by the individual photo diodes of the sensing means. In the horizontal dimension the diagram represents a time in seconds. The diagram shows four different curves 26*a*, 26*b*, 26*c* and 26*d*, representing voltage signals created by the four photo diodes (16*a*-16*d*, respectively, in FIGS. 3-6).

The curves have been recorded from a light device as described in FIG. 3. The light device was placed with the light output over a physical model of a patient's dentition. In section A of the diagram the light device was deactivated (switched off). Accordingly, the photo diodes created only a low output signal which was caused by ambient light received by the photo diodes. Section B represents a time-period of about 12 seconds in which the light device was activated (switched on). Accordingly, the photo diodes created significantly higher output signals compared to the signals in section A. In a first partial time-period C (or section C) of the time-period B the light device was held in a position to irradiate a molar in the dentition model. The photo diodes each created approximately constant output signals, although the magnitude of the output signals were different. At the beginning of a second partial time-period D (or section D) the light device was repositioned and held in a position to only partly irradiate the molar. In practice such a positioning may cause a dental filling material placed in the molar to be insufficiently irradiated and thus may cause that material to insufficiently harden. Such a positioning may therefore be designated as a malposition for hardening the dental material. As apparent from the diagram in the transition between sections C and D the output signals generated by two of the photo diodes significantly change. These signal changes are indicative of a change of the position of the light device and can be used to indicate the position change, for example by activating a vibrating alert of the device. In a third partial time-period E the light device was positioned back to generally the position the light device was positioned during time-period C. As apparent from the diagram the output signals in sections E and C generally correspond to each other, while at least some of the output signals in section D are significantly different. Accordingly it was shown that a change of the position of the light device can be recognized in a reproducible manner via the photo sensors.

There are several options to automatically recognize a signal change or position change as illustrated. In one option the output signals of each of the photo diodes are monitored over time. Such a change can for example be determined if a recently measured output signal is significantly different than the previously measured output signal. Therefore, over a time-period a series of 1 to n measurements of output signals $S_1$ to $S_n$ may be performed. Each output signal $S_i$ may be measured at a time $T_i$ so that pairs of values $S_i$; $T_i$ may be stored in a controller of the device, wherein i=1 to n. A threshold ΔS may be used to evaluate whether an output signal $S_i$ is within a desired limit. This is case if the condition $S_i<S_{i-1}+\Delta S$ and the condition $S_i>S_{i-1}-\Delta S$ each are fulfilled. Optionally, an average output signal $S_{Av}$ may be formed from a number of output signals $S_{i-k}$ to $S_{i-1}$, with k being 2 or more. In this case the evaluation of whether the output signal $S_i$ is within the desired range can be determined from checking the conditions $S_i<S_{Av}+\Delta S$ and $S_i>S_{Av}-\Delta S$.

In the present example the threshold ΔS may be about 20 mV. The output signal of the photo diode $S_3$ is about 230 mV at the time $T_3$ and $S_4$ is about 170 mV at the time $T_4$. The condition $S_4<S_3+\Delta S$ or 170 mV<230 mV+20 mV or 170 mV<250 mV is fulfilled. However the condition $S_4>S_3-\Delta S$ or 170 mV>230 mV−20 mV or 170 mV>210 mV is not fulfilled. Hence $S_4$ is outside the desired limits so that a position change is indicated by the device.

Although in the present example a vibrating alert is used, other indicators may be used such as an audio or visual feedback device, or a combination thereof. An audio feedback device may for example comprise a piezo pulse emitter or loudspeaker and may indicate a position change by a beep or other appropriate sound. Further, a visual feedback device may comprise a light source, for example an LED which indicates a position change by flashing or glowing, for example.

The light device of all embodiments preferably has an electronic controller which is electrically connected or connectable with the photo diodes for receiving an output signal from each of the photo diodes. The controller is preferably further configured to monitor the output signals over time and to evaluate whether a position change occurred for example in a way as for example described above. The controller may be activated upon activating the light device.

Although in the examples than four photo diodes are used for sensing changes of the position of the light device in four directions (or two dimensions), more than four photo diodes may be used. In one example, one or more CCD or CMOS imaging devices are used for sensing changes of the position of the light device.

What is claimed is:

1. A dental light irradiation device for irradiating a light hardenable dental material, comprising:
    a light source for emitting blue light in a wavelength range suitable to cure the light hardenable dental material;
    an indicator activated in response to a detected position change of the device with respect to the light hardenable dental material, wherein the indicator comprises a vibrating alert device, an audio or visual feedback device, or a combination thereof;
    a sensor that detects a light intensity and generates a signal corresponding to the detected light intensity, the signal indicative of a position of the device with respect to the light hardenable dental material; and
    a controller that determines whether a difference between a first value of the signal measured at a first time and a second value of the signal measured at a second, subsequent time is indicative of a position change of the device with respect to the light hardenable dental material that satisfies a predetermined threshold, and activates the indicator upon determining that the position change of the device with respect to the light hardenable dental material satisfies the predetermined threshold.

2. The device of claim 1, further comprising a database holding one or more patterns that are indicative of a position change of the device with respect to the light hardenable dental material, the one or more patterns being in the form of data sets of physical quantities, wherein the physical quantities are light intensities as detectable by the sensor during operation of the device, and wherein the controller is further configured to compare a plurality of signals generated by the sensor with the one or more patterns to determine whether the position change with respect to the light hardenable dental material resulted from activation of the device by the user.

3. The device of claim 1, wherein the controller updates a previous one of the signal values with a current signal value to determine a reference position of the device.

4. The device of claim 1, wherein the controller updates a reference value with an average of two or more signal values generated by the sensor and compares a current signal value generated by the sensor to the reference signal value to determine whether the position change satisfies the predetermined threshold.

5. The device of claim 1, further comprising a light guide comprising a light input at one end and a light output on an opposite end, the light guide being configured for guiding light incident on one of the ends to the respective other one of the ends via reflection, in particular via total reflection.

6. The device of claim 5, wherein the light guide comprises a plurality of optical fibers extending parallel between the light input and the light output.

7. The device of claim 1, wherein the sensor comprises one or more photodiodes and the device further comprises a light guide formed of a multiplicity of fibers extending parallel from the light source to a light output, the light guide configured for guiding the emitted blue light within a body of the device from the light source towards a light output, the light output forming a planar surface, the one or more photodiodes arranged adjacent the light output.

8. The device of claim 7, wherein the one or more photodiodes form a circumferential ring surrounding the light output.

9. The device of claim 2, wherein activation of the device by the user includes operation of an on/off button.

10. The device of claim 1, wherein the controller leaves the indicator inactivated upon determining that the position change of the device with respect to the light hardenable dental material resulted from activation of the device by the user.

* * * * *